(12) United States Patent
Matoba et al.

(10) Patent No.: US 10,054,555 B2
(45) Date of Patent: Aug. 21, 2018

(54) X-RAY TRANSMISSION INSPECTION APPARATUS AND INSPECTION METHOD USING THE SAME

(71) Applicant: HITACHI HIGH-TECH SCIENCE CORPORATION, Tokyo (JP)

(72) Inventors: Yoshiki Matoba, Tokyo (JP); Akihiro Takeda, Tokyo (JP); Shingo Tsuboi, Tokyo (JP); Toshihiro Sakai, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 231 days.

(21) Appl. No.: 15/220,880

(22) Filed: Jul. 27, 2016

(65) Prior Publication Data

US 2017/0031054 A1 Feb. 2, 2017

(30) Foreign Application Priority Data

Jul. 29, 2015 (JP) .................................. 2015-149138

(51) Int. Cl.
*G01N 23/04* (2018.01)
*G01S 17/08* (2006.01)

(52) U.S. Cl.
CPC ......... *G01N 23/04* (2013.01); *G01N 2223/50* (2013.01); *G01N 2223/652* (2013.01); *G01S 17/08* (2013.01)

(58) Field of Classification Search
CPC ............... G01N 23/04; G01N 2223/50; G01N 2223/652; G01S 17/08
See application file for complete search history.

(56) References Cited

U.S. PATENT DOCUMENTS

| 5,664,001 A * | 9/1997 | Tachibana | ................ A61B 6/14 378/108 |
| 9,863,896 B2 * | 1/2018 | Matoba | ................ G01N 23/083 |
| 2015/0276626 A1 * | 10/2015 | Matoba | ................ G01N 23/083 378/69 |
| 2016/0004062 A1 * | 1/2016 | Dixon | .................... G02B 21/36 348/80 |

FOREIGN PATENT DOCUMENTS

JP 2004257884 9/2004

* cited by examiner

*Primary Examiner* — Mark R Gaworecki
(74) *Attorney, Agent, or Firm* — Hamre, Schumann, Mueller & Larson, P.C.

(57) ABSTRACT

Disclosed are an X-ray transmission inspection apparatus and an inspection method using the same that are capable of preventing over-detection and erroneous detection of foreign matter even when variations in vertical position of the sample occur. The X-ray transmission inspection apparatus includes: an X-ray source (2) irradiating a sample with X-rays; a sample moving device (3) moving the sample S continuously to a predetermined direction while X-rays X are emitted from the X-ray source; a time delay integration sensor (TDI sensor) (4) provided opposed to the X-ray source based on the sample, and detecting the X-rays transmitted through the sample; a distance sensor (5) measuring a distance between the X-ray source and the sample; and a TDI controller (6) controlling the TDI sensor by changing a charge transfer speed of the TDI sensor (4) in real time based on variations in the distance measured by the distance sensor.

4 Claims, 2 Drawing Sheets

X-RAY TRANSMISSION INSPECTION APPARATUS AND INSPECTION METHOD USING THE SAME

CROSS REFERENCE TO RELATED APPLICATION(S)

The present application claims priority to Japanese Patent Application No. 2015-149138, filed Jul. 29, 2015, the entire contents of which is incorporated herein for all purposes by this reference.

BACKGROUND OF THE INVENTION

1. Technical Field

The present invention relates generally to an X-ray transmission inspection apparatus and an inspection method using the same, the apparatus and method being capable of detecting minute foreign matter in a sample. More particularly, the present invention relates to an X-ray transmission inspection apparatus and inspection method using the same, the apparatus and method being capable of detecting foreign matter smaller than tens of μm in size in a sample.

2. Description of the Related Art

Generally, to detect foreign matter, such as a minute metal particle, in a sample, X-ray transmission inspection is used on the sample by means of an X-ray transmission image that is obtained by irradiating a sample with X-rays. For example, in a lithium-ion secondary battery, which has been recently applied to an automobile, a hybrid vehicle, an electric vehicle, or the like, an electrode, as an anode, of the lithium-ion secondary battery is formed in such a manner that a lithium manganese oxide film or a lithium cobalt oxide film is formed on both surfaces of an Al film. Due to this, when foreign matter, such as Fe (iron) or SUS (stainless), having a size of tens of μm or larger is mixed into the battery, a short circuit may occur, causing a decrease in performance or even ignition of the battery. Therefore, there is a demand in the lithium-ion secondary battery that a battery with a foreign matter mixed therein during production be detected and removed in advance.

As an X-ray transmission inspection apparatus for detecting foreign matter or the like in a sample is well-known. In such an inspection apparatus, during inspection, an X-ray source and an X-ray detector, such as a line sensor, face each other, and a sample moving in one direction is disposed therebetween. As an example, patent document 1 discloses an X-ray inspection apparatus for detecting a foreign matter, the apparatus capable of detecting even minute foreign matter with high sensitivity using a time delay integration sensor (TDI sensor).

The X-ray inspection apparatus, which is mentioned above, includes: an X-ray image intensifier (image intensity amplifier: IIF); a TDI sensor performing the functions of synchronizing an X-ray transmission image moving on an imaging surface of the X-ray image intensifier with a charge transfer speed of the TDI sensor; enlarging an image photographed on an input screen of the X-ray image intensifier in accordance with a belt conveyor velocity V by an optical enlargement ratio b/a, which is calculated based on a distance b from the X-ray source to a foreign matter (in effect, to the belt conveyor) and a distance a from the X-ray source to the input screen of the X-ray image intensifier; and calculating a velocity V3, as a moving velocity of an image of the foreign matter created by the TDI sensor, by multiplying the conveyor belt velocity V, b/a, and the rest.

In other words, in the conventional X-ray inspection apparatus for detecting foreign matter, an optical enlargement ratio, which is calculated both by synchronizing a moving velocity of the sample with the charge transfer speed of the TDI sensor, and by a ratio of a predetermined distance (FOD) between from the X-ray source to the foreign matter (in effect, to a mounting surface of a belt conveyor) to a distance (FDD) from the X-ray source to the X-ray detector: FDD/FOD, is set as a correction factor.

The foregoing is intended merely to aid in the understanding of the background of the present invention, and is not intended to mean that the present invention falls within the purview of the related art that is already known to those skilled in the art.

DOCUMENT OF RELATED ART

Patent Document

Patent Document 1: Japanese Patent Application Publication No. 2004-257884.

SUMMARY OF THE INVENTION

The related art mention above poses the following problem.

In other words, in the conventional X-ray transmission inspection apparatus, even though a charge transfer speed of a time delay integration sensor (TDI sensor) is determined in consideration of an optical enlargement ratio, inspection is performed under the constant charge transfer speed. For this reason, in the case where variations in vertical position of the sample occur while the sample moves, a focus location of an X-ray transmission image on a detection surface of the TDI sensor is changed. Due to this, even though the same foreign matter in the same sample is detected, a different in degree of calculating the detected signal by the TDI sensor occurs, and a blur of an image may occur. Consequently, when variations in the vertical position of the sample occur, over-detection and erroneous detection of the foreign matter in the sample may occur.

Accordingly, the present invention has been made keeping in mind the above problems occurring in the related art, and the present invention is intended to propose an X-ray transmission inspection apparatus and an inspection method using the same, whereby the apparatus and method are capable of preventing over-detection and erroneous detection of foreign matter even when variations in vertical position of the sample occur.

In order to achieve the above object, according to one aspect of the present invention, there is provided an X-ray transmission inspection apparatus including: an X-ray source irradiating a sample with X-rays; a sample moving device moving the sample continuously in a predetermined direction while X-rays are emitted from the X-ray source; a time delay integration sensor (TDI sensor) provided opposed to the X-ray source with regard to the sample, and detecting the X-rays transmitted through the sample; a distance sensor measuring a distance between the X-ray source and the sample; and a TDI controller controlling the TDI sensor by changing a charge transfer speed of the TDI sensor in real time based on variations in the distance measured by the distance sensor.

In the X-ray transmission inspection apparatus, the TDI sensor is controlled by changing a charge transfer speed of the TDI sensor in real time based on variations in the distance measured by the distance sensor while the sample moves, whereby variations in the distance are detected in real time, and the variations are promptly reflected in determining the charge transfer speed, and thus it is possible to prevent a blur of an image by adjusting the focus of the X-ray transmission image. Further, as a physical action is not required in the present invention, the charge transfer speed of the TDI sensor can be swiftly changed in real time, and the time, which is required to control the TDI sensor so as to deal with the variations, is short. Thereby, it is possible to shorten intervals of data acquisition, and it is possible to acquire more detailed data, and thus it is possible to adjust a location of the sample with high degree of precision.

In the X-ray transmission inspection apparatus, the sample may be in a band shape, and the distance sensor may be a laser distance sensor configured to measure the distance based on reflection of a laser beam projected onto the sample, wherein the laser beam is projected onto the sample in a direction crossing a moving direction of the sample and in a linear spot shape extending in a width direction of the sample.

In other words, in the X-ray transmission inspection apparatus, the distance sensor is configured such that the laser beam is projected onto the sample in a direction crossing a moving direction of the sample and in a linear spot shape extending in a width direction of the sample, thereby realizing two-dimensional detection, and thus it is possible to recognize positional variations in a wide area and possible to improve precision.

In order to achieve the above object, according to one aspect of the present invention, there is provided an X-ray transmission inspection method including: irradiating a sample with an X-ray generated from an X-ray source; moving the sample continuously in a predetermined direction while X-rays are emitted from the X-ray source; detecting the X-rays transmitted through the sample using a time delay integration sensor (TDI sensor) provided opposed to the X-ray source with regard to the sample; measuring a distance between the X-ray source and the sample using a distance sensor; and controlling the TDI sensor by changing a charge transfer speed of the TDI sensor in real time based on variations in the distance measured by the distance sensor.

In the X-ray transmission inspection method, the sample may be in a band shape, and the distance sensor may be a laser distance sensor configured to measure the distance based on reflection of a laser beam projected onto the sample, wherein the laser beam is projected onto the sample in a direction crossing a moving direction of the sample and in a linear spot shape extending in a width direction of the sample.

According to the present invention, advantageous effect is as follows.

In the X-ray transmission inspection apparatus and the inspection method using the same according to the present invention, the TDI sensor is controlled by changing a charge transfer speed of the TDI sensor in real time based on variations in the distance measured by the distance sensor, and thus it is possible to prevent a blur of an X-ray transmission image by adjusting the focus of the X-ray transmission image. Therefore, even when variations in vertical position of the sample occur, it is possible to prevent over-detection and erroneous detection of the foreign matter.

BRIEF DESCRIPTION OF THE DRAWINGS

The above and other objects, features and other advantages of the present invention will be more clearly understood from the following detailed description when taken in conjunction with the accompanying drawings, in which.

DESCRIPTION OF THE PREFERRED EMBODIMENTS

Hereinafter, an embodiment of an X-ray transmission inspection apparatus and an inspection method using the same according to the present invention will be described with reference to FIGS. 1 to 3.

Figure 1:
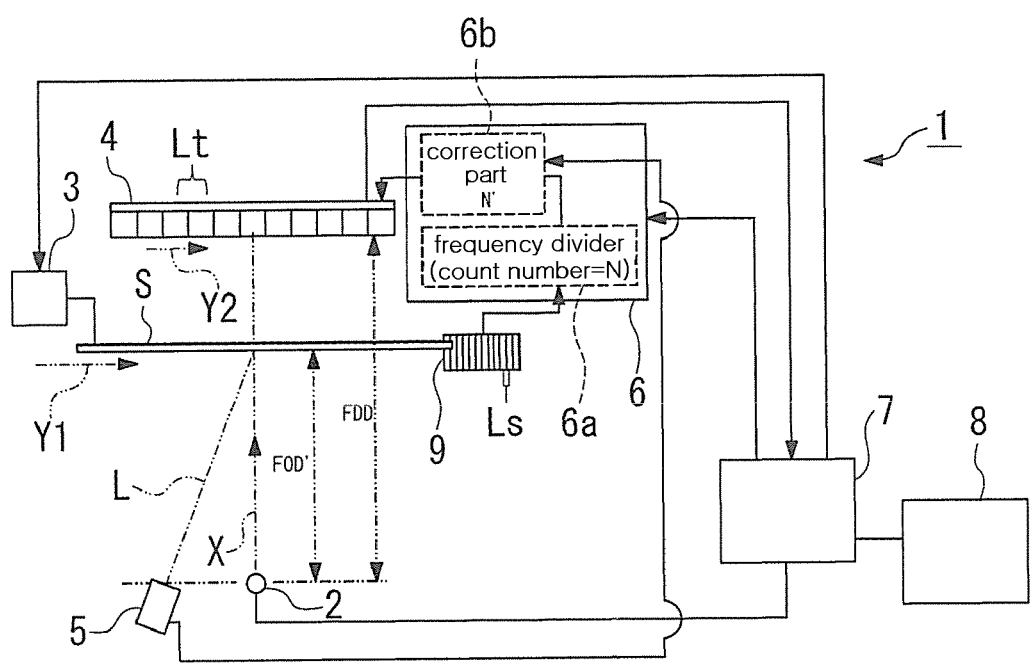
FIG. 1 is a schematic view illustrating an X-ray transmission inspection apparatus and an inspection method using the same according to a first embodiment of the present invention.

As shown in FIG. 1, the X-ray transmission inspection apparatus according to the embodiment includes: an X-ray source 2 irradiating a sample S with X-rays; a sample moving device 3 moving the sample S continuously in a predetermined direction while X-rays X are emitted from the X-ray source 2; a time delay integration sensor (TDI sensor) 4 provided opposed to the X-ray source 2 with respect to the sample S, and detecting the X-rays transmitted through the sample S; a distance sensor 5 measuring a distance between the X-ray source 2 and the sample S; and a TDI controller 6 controlling the TDI sensor 4 by changing a charge transfer speed of the TDI sensor 4 in real time based on variations in the distance measured by the distance sensor 5 while the sample S moves.

Further, the X-ray transmission inspection apparatus 1 according to the embodiment further includes: a main controller 7 controlling the above elements by being connected thereto; and a display unit 8 displaying a transmission image that indicates a distribution of intensity of the detected transmission X-ray.

The main controller 7 is a computer including a CPU, or the like. A processing circuit that creates a transmission image by processing an image based on signals input from the TDI sensor 4, and displays the image on the display unit 8 is included.

The display unit 8 is a display device that displays a contrast image or the like by being connected to the main controller 7. The display unit 8 is capable of displaying a variety of different information in accordance with a control of the main controller 7.

The X-ray source 2 is a Roentgen tube capable of emitting X-rays X, which are generated when thermoelectrons generated from a filament (anode) in the tube are accelerated by a voltage applied between the filament (anode) and a target (cathode) to collide against the target, such as W (tungsten), Mo (molybdenum), Cr (chrome), or the like, as a primary X-ray from a window of beryllium foil or the like.

The sample S is, for example, in a band shape, and is used for lithium-ion battery or medical use. The sample S is, for example, an electrode sheet used in a lithium-ion secondary battery, and the foreign matter is, for example, Fe or SUS that may be mixed in the electrode as foreign matter.

The sample moving device 3 is, for example, a motor capable of moving in an extension direction of the sample S relative to the TDI sensor 4. The sample moving device 3 is provided with at least a pair of rollers (not shown) that move the sample S in the extension direction through a roll-to-roll method.

Further, the sample moving device 3 is provided with a linear scale 9 to quantify a moving distance of the sample S, and the moving distance of the sample S can be calculated by pitch Ls of the scale.

Figure 2:
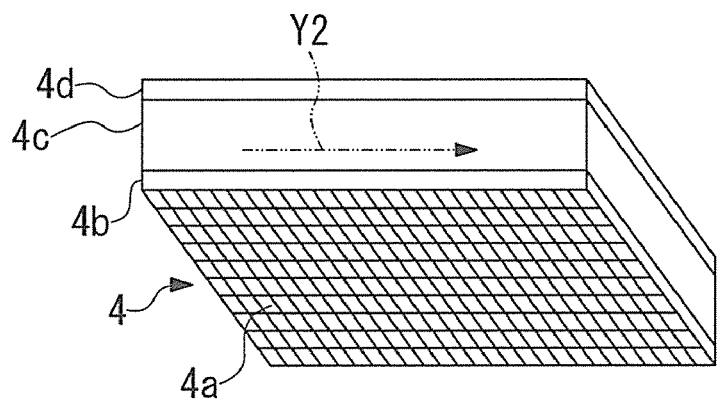
FIG. 2 is a perspective view illustrating a TDI sensor according to the first embodiment.

As shown in FIG. 2, the TDI sensor 4 is an X-ray detector configured such that a plurality of cells (sensor elements) is placed in a direction perpendicular to the moving direction of the sample S and placed in a direction in parallel thereto. The TDI sensor includes: a phosphor 4b disposed on a detection surface 4a; a FOP (fiber optics plate) 4c configured such that a plurality of optical fibers is arranged two-dimensionally beneath the phosphor 4b; a Si photodetector 4d disposed beneath the FOP 4c; and line sensors arranged in multiple rows. For example, the TDI sensor 4 may be configured such that the unit line sensors of 200~1000 are arranged in the moving direction of the sample S.

In the TDI sensor 4, CsI (cesium iodide), GOS (gadolinium oxysulfide), or YAG (yttrium aluminum garnet) is used as the phosphor 4b.

Further, the TDI sensor 4 is configured such that charge accumulation and charge transfer are performed in a sensor pitch Lt. A line rate is usually 0.5~100 kHz.

The distance sensor 5 is a reflection-type laser distance sensor configured to measure the distance based on reflection of a laser beam L projected onto the sample S. The distance sensor 5 is provided next to the X-ray source 2 so as to be opposed to the sample S, and projects the laser beam L onto the sample S in a spot shape, as a dot shape, wherein the distance between the sample S and the X-ray source 2 is measured based on the reflected beam mainly using trigonometry. Further, the distance measurement result from the distance sensor 5 is sent to the TDI controller 6.

The distance sensor 5 has repeated-measurement precision of about 0.01 μm, a response frequency of more than 300 kHz, and a sampling time of tens of μs, and thus it is possible to measure a distance in a very short time with high degree of precision.

Figure 3:
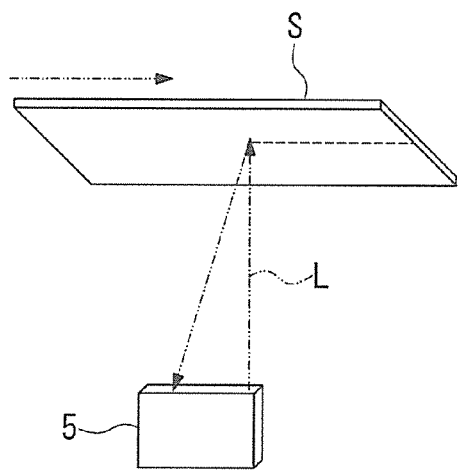
FIG. 3 is a view illustrating a method of measuring distance using a distance sensor according to the first embodiment.

In the distance sensor 5, although the spot shape is a dot shape, a point of the laser beam L is taken on the moving sample S, and thereby, as shown in FIG. 3, it is possible to measure a distance in one-dimension (a linear shape). Here, a measurement interval of the distance FOD' between the sample S and the X-ray source 2 is determined based on both a response time of the distance sensor 5 and a response time of the charge transfer speed of the TDI sensor 4.

Further, the distance sensor 5 may be a distance sensor utilizing other principles that are capable of achieving the same object.

The TDI controller 6 adjusts a direction and velocity of the charge transfer of the TDI sensor 4 to the moving direction and velocity of the sample S, and also calculates luminance of the X-rays X that are incident on an incidence surface 4a of the TDI sensor 4.

In other words, the TDI controller 6 performs a control, as a control in a case where variations in vertical position of the sample S do not occur, in a manner that velocity (charge transfer speed) $V_{TDI}$ and the direction of the charge transfer in a detection range of the TDI sensor 4 is set to be equal to velocity Vs and the moving direction of the sample S, and a flow of the sample S is synchronized with calculating process of the TDI sensor 4.

Further, arrow Y1 in the drawings denotes the moving direction of the sample S, and arrow Y2 denotes a TDI operational direction of the TDI sensor 4.

Further, the TDI controller 6 determines an enlargement ratio of the TDI sensor 4 (an enlargement ratio when an image of the sample S is projected onto the incidence surface 4a), and controls the TDI sensor 4 based on the enlargement ratio.

In other words, TDI controller 6 includes: a frequency divider 6a calculating the enlargement ratio N of the TDI sensor 4; and a correction part 6b correcting the enlargement ratio N calculated by the frequency divider 6a into a corrected enlargement ration N' and calculating a charge transfer speed based on a corrected velocity of the sample S that is corrected based on the corrected enlargement ratio N'.

The frequency divider 6a calculates the enlargement ratio N of the TDI sensor 4 as a fixed value on the basis of a ratio of the pitch Ls of the linear scale 9 measuring the moving distance of the sample S to TDI pitch Lt of the TDI sensor 4: Lt/Ls, and sends the enlargement ratio to the correction part 6b.

The enlargement ratio N is a fixed value, and calculated by the following relationship: N=(Lt/Ls)×(FOD/FDD). Here, the FOD is a fixed value and refers to the distance between the sample S and the X-ray source 2 in a case where variations in vertical position of the sample do not occur.

Further, the frequency divider 6a may include a circuit that add a signal of frequency f1, and obtains an output of frequency f2 (f2=f1/n, n:integer) by being in sync therewith, and serves to decrease frequency to 1/integer using a counting circuit of a digital integrated circuit (IC).

The correction part 6b corrects the enlargement ratio N from the frequency divider 6a on the basis of a factor of the ratio of the distance FOD' between the sample S and the X-ray source 2 calculated in real time by the distance sensor 5 to the distance FDD, as a fixed value, between the X-ray source 2 and the incidence surface 4a: FOD'/FDD; determines the charge transfer speed of the TDI sensor 4 on the basis of the corrected enlargement ratio N'; and sends the information to the TDI sensor 4.

The corrected enlargement ratio N' is calculated in real time by the following relationship accompanied by variations in the distance FOD' that is calculated at all times: N'=(Lt/Ls)×(FOD'/FDD). Here, "real time" is determined by the line rate of the TDI sensor 4 and the sampling time of the distance sensor 5, wherein by making the sampling time of the distance sensor 5 as short as possible, it is possible to realize a control with high degree of precision.

Next, reference will be made to an X-ray transmission inspection method using the X-ray transmission inspection apparatus according to the embodiment. In the X-ray transmission inspection method, for example, the sample S is an anode sheet of the lithium-ion secondary battery, and the foreign matter therein is detected.

First of all, the sample S is moved between the X-ray source 2 and the TDI sensor 4 at a predetermined velocity by the sample moving device 3. Further, a thickness of the sample S is much smaller compared with the distance between the sample S and the TDI sensor 4.

Then, the distance FOD' between the sample S and the X-ray source 2 is calculated based on the measurement result from the distance sensor 5.

Next, X-ray source 2 emits the X-rays X to the sample S, and the transmission X-ray transmitted through the sample S and the foreign matter is detected by the TDI sensor 4. Further, as the sample S is moved in a predetermined direction by the sample moving device 3, the sample S in a moving direction is entirely scanned to obtain an entire intensity distribution of the transmission X-ray.

Further, the intensity distribution of the transmission X-ray is subject to image processing by the main controller 7, and thereby a transmission image is created and displayed on the display unit 8. Here, the X-ray transmission amount varies between a site where the foreign matter is present and a site where the foreign matter is not present, whereby the contrast of the site where the foreign matter is present is different from that in the other sites, and thus presence of the foreign matter is detected.

In the case where the sample S is moved, for example, when the sample S moves upward due to the state of sample moving device 3 whereby the vertical position of the sample S is changed, the distance FOD' between the sample S and the X-ray source 2 is increased. Here, a contrast and intensity distribution caused by foreign matter is the reason for the size variation of the X-ray generation point. As a result, it is difficult for a conventional apparatus which does not comprise equipment to counteract the change, to recognize the degree of the contrast caused by the foreign matter and the foreign matter cannot be detected.

However, in the embodiment, the correction part 6b corrects the enlargement ratio N and calculates a corrected enlargement ratio N' by means of an enlargement ratio N calculated by the frequency divider 6a based on both the distance FOD' between the sample S and the X-ray source 2, which is measured in real time by the distance sensor 5, and the moving distance of the sample S, which is measured by the linear scale 9. The TDI controller 6 determines a charge transfer speed of the TDI sensor 4 based on the corrected enlargement ratio N' and controls the TDI sensor 4.

In other words, given that an initial charge transfer speed is v, a changed charge transfer speed v' is calculated by the relationship: $v'=v \times (FOD'/FDD)$. Thus, the TDI controller 6 controls the TDI sensor 4 by means of the charge transfer speed v'.

Thereby, when a focus location of an image that is input to the TDI sensor 4 is changed by the change in vertical position of the sample S, it is possible to realize a best focus location by adjusting a charge transfer speed.

Therefore, the distance FOD' is measured at all times by the distance sensor 5, and the charge transfer speed of the TDI sensor 4 is corrected based on the corrected enlargement ratio N', which is corrected in accordance with a change in distance, and thereby when variations in vertical position of the sample S occur by moving upward or downward, a blur in the X-ray transmission image does not occur, and thus it is possible to detect foreign matter with a high degree of precision.

In the X-ray transmission inspection apparatus 1 according to the embodiment and the inspection method using the same, the TDI sensor 4 is controlled by changing a charge transfer speed of the TDI sensor 4 in real time based on variations in the distance FOD' measured by the distance sensor 5 while the sample S moves, whereby variations in the distance FOD' are detected in real time, and the variations are promptly reflected in determining the charge transfer speed, and thus it is possible to prevent a blur of an image by adjusting the focus of the X-ray transmission image.

Further, as a physical action is not required in the present invention, the charge transfer speed of the TDI sensor 4 can be swiftly changed in real time, and the time, which is required to control the TDI sensor so as to deal with the variations, is short. Thereby, it is possible to shorten intervals of data acquisition, and it is possible to acquire more detailed data, and thus it is possible to adjust a location of the sample S with a high degree of precision.

Figure 4:
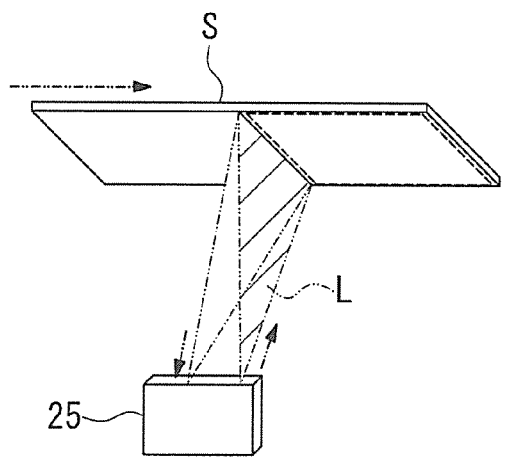
FIG. 4 is a view illustrating a method of measuring distance using the distance sensor in the X-ray transmission inspection apparatus and the inspection method using the same according to a second embodiment of the present invention.

Next, a second embodiment of the X-ray transmission inspection apparatus and the inspection method using the same according to the present invention will be described hereinafter with reference to FIG. 4. Further, throughout the drawings, the same reference numerals as the above will refer to the same or like parts and detailed descriptions thereof will be omitted.

The difference between the first embodiment and the second embodiment is as follows. In the first embodiment, as shown in FIG. 3, the laser beam L of the distance sensor 5 is in a spot shape, as a dot shape, and performs a one-dimensional measurement on the moving sample S in a line. On the contrary, in the second embodiment, as shown in FIG. 4, the X-ray transmission inspection apparatus and the inspection method using the same, a laser beam L of a distance sensor 25 is in a linear shape, and performs a two-dimensional measurement on the moving sample S by area.

In other words, in the second embodiment, the distance sensor 25 is configured such that the laser beam L is projected onto the sample S in a direction crossing a moving direction of the sample S and in a linear spot shape extending in a width direction of the sample S.

For example, the laser beam L of the distance sensor 25 is in a linear spot shape having a width ranging from tens of mm to tens of μm, measures the distance from the distance sensor 25 to a measurement location within the range of several mm to tens of mm, and is optimally disposed when necessary.

Thus, in the X-ray transmission inspection apparatus and the inspection method using the same according to the second embodiment, the distance sensor 25 is configured such that the laser beam L is projected onto the sample S in a direction crossing a moving direction of the sample S and in a linear spot shape extending in a width direction of the sample S, thereby realizing two-dimensional detection, and thus it is possible to recognize positional variations in a wide area and possible to improve precision.

Further, the above embodiments of the present invention have been described for illustrative purposes, and those skilled in the art will appreciate that various modifications, additions and substitutions are possible, without departing from the scope and spirit of the invention as disclosed in the accompanying claims.

For example, the linear scale 9 for quantifying a moving distance of the sample S may be a rotary encoder, which works as the linear scale.

Further, in the embodiment, the enlargement ratio N is calculated by the frequency divider 6a based on the moving distance of the sample S measured by the linear scale 9; however, the enlargement ratio N may be calculated based on a driving signal indicated by the sample moving device 3 (a motor, or the like not shown in the drawings) that causes the moving distance of the sample S.

Further, an area sensor may be used as the distance sensor 25 according to the second embodiment. The area sensor may be configured to be in a two-dimensional spot shape, or to be in a spot shape formed by arranging a plurality of linear sensors. Thanks to use of the area sensor, it is possible to obtain the distance measurement result with high degree of precision.

What is claimed is:

1. An X-ray transmission inspection apparatus comprising:
   an X-ray source irradiating a sample with X-rays;
   a sample moving device moving the sample continuously in predetermined direction while X-rays are emitted from the X-ray source;
   a time delay integration sensor (TDI sensor) provided opposed to the X-ray source with respect to the sample, and detecting the X-rays transmitted through the sample;
   a distance sensor measuring a distance between the X-ray source and the sample; and
   a TDI controller controlling the TDI sensor by changing a charge transfer speed of the TDI sensor in real time based on variations in the distance measured by the distance sensor.

2. The X-ray transmission inspection apparatus of claim 1, wherein
   the sample is in a band shape, and
   the distance sensor is a laser distance sensor configured to measure the distance based on reflection of a laser beam projected onto the sample, wherein the laser beam is projected onto the sample in a direction crossing a moving direction of the sample and in a linear spot shape extending in a width direction of the sample.

3. An X-ray transmission inspection method comprising:
   irradiating a sample with X-rays generated from an X-ray source
   moving the sample continuously in a predetermined direction while X-rays are emitted from the X-ray source;
   detecting the X-rays transmitted through the sample using a time delay integration sensor (TDI sensor) provided opposed to the X-ray source with respect to the sample;
   measuring a distance between the X-ray source and the sample using a distance sensor; and
   controlling the TDI sensor by changing a charge transfer speed of the TDI sensor in real time based on variations in the distance measured by the distance sensor.

4. The X-ray transmission inspection method of claim 3, wherein
   the sample is in a band shape, and
   the distance sensor is a laser distance sensor configured to measure the distance based on reflection of a laser beam projected onto the sample, wherein the laser beam is projected onto the sample in a direction crossing a moving direction of the sample and in a linear spot shape extending in a width direction of the sample.

* * * * *